United States Patent [19]
Sloman

[11] Patent Number: 6,101,416
[45] Date of Patent: Aug. 8, 2000

[54] SYSTEM AND METHOD FOR ATRIAL AUTOCAPTURE IN SINGLE-CHAMBER PACEMAKER MODES USING FAR-FIELD DETECTION

[75] Inventor: Laurence S. Sloman, Los Angeles, Calif.

[73] Assignee: Pacesetter, Inc., Sylmar, Calif.

[21] Appl. No.: 09/124,811

[22] Filed: Jul. 29, 1998

[51] Int. Cl.⁷ .................................................. A61N 1/368
[52] U.S. Cl. .................................. 607/28; 607/9; 600/509
[58] Field of Search ................................... 607/28, 9, 27, 607/62; 600/509, 521

[56] References Cited

U.S. PATENT DOCUMENTS

| | | |
|---|---|---|
| 4,940,052 | 7/1990 | Mann et al. . |
| 4,944,298 | 7/1990 | Sholder . |
| 5,458,623 | 10/1995 | Lu et al. . |
| 5,476,486 | 12/1995 | Lu et al. . |
| 5,683,426 | 11/1997 | Greenhut et al. ............................. 607/9 |
| 5,766,225 | 6/1998 | Kramm ....................................... 607/4 |

OTHER PUBLICATIONS

Levine, et al; Assessment of Atrial Capture in Committed Atrioventricular Sequential (DVI) Pacing Systems; pp 616–623; Pace vol. 6, May–Jun. 19983, Part 1.

Levine, et al; Confirmation of Atrial Capture and Determination of Atrial Capture Thresholds in DDD Pacing Systems; pp 465–473; Clin. Prog. Pacing and Electrophysiol. 1984, vol. 2, No. 5.

Brandt, et al; Far–Field ORS Complex Sensing Via the Atrail Pacemaker Lead. I. Mechanism, Consequences, Differential Diagnoisis and Countermeasures in AAI and VVD/DDD Pacing; pp 1432–14738; Pace vol. 11. Oct. 1988.

Levine; Guidelines to the Routine Evaluation and Follow–Up of the Implanted Pacing System; pp 19; Siemens Pacesetter; Jan. 1993.

*Primary Examiner*—Kennedy J. Schaetzle

[57] ABSTRACT

An implantable pacemaker automatically verifies atrial capture and performs atrial stimulation energy assessment when atrial capture is absent. The pacemaker delivers a stimulation pulse in the atrial chamber of the heart and samples the resulting far-field signal from the ventricular chamber during a predetermined far-field interval window. The pacemaker then compares the far-field signal sample to a predetermined far-field signal recognition template. If the far-field signal sample is approximately equal to the far-field signal recognition template, then atrial capture is deemed verified; otherwise, the pacemaker performs an atrial stimulation energy determination. Optionally, the pacemaker automatically determines the timing of the far-field interval window and defines the far-field signal recognition template.

30 Claims, 5 Drawing Sheets

SYSTEM AND METHOD FOR ATRIAL AUTOCAPTURE IN SINGLE-CHAMBER PACEMAKER MODES USING FAR-FIELD DETECTION

FIELD OF THE INVENTION

The present invention relates in general to implantable cardiac stimulation devices, including bradycardia and anti-tachycardia pacemakers, defibrillators, cardioverters and combinations thereof that are capable of measuring physiological data and parametric data pertaining to implantable medical devices. More particularly, this invention relates to a system and method for automating detection of atrial capture in an implantable cardiac stimulation device using far-field signal detection.

BACKGROUND OF THE INVENTION

Implantable medical devices, such as pacemakers, defibrillators, and cardioverters (collectively referred to herein as implantable cardiac stimulating devices), are designed to monitor and stimulate the heart of a patient that suffers from a cardiac arrhythmia. Using leads connected to a patient's heart, these devices typically stimulate the cardiac muscles by delivering electrical pulses in response to measured cardiac events that are indicative of a cardiac arrhythmia. Properly administered therapeutic electrical pulses often successfully reestablish or maintain the heart's regular rhythm.

Implantable cardiac stimulating devices can treat a wide range of cardiac arrhythmias by using a series of adjustable parameters to alter the energy, shape, location, and frequency of the therapeutic pulses. The adjustable parameters are usually defined in a computer program stored in a memory of the implantable device. The program (which is responsible for the operation of he implantable device) can be defined or altered telemetrically by a medical practitioner using an external implantable device programmer.

Modern programmable pacemakers, the most commonly used implantable devices, are generally of two types: (1) single-chamber pacemakers, and (2) dual-chamber pacemakers. In a single-chamber pacemaker, the pacemaker provides stimulation pulses to, and senses cardiac activity within, a single-chamber of the heart (e.g., either the right ventricle or the right atrium). In a dual-chamber pacemaker, the pacemaker provides stimulation pulses to, and senses cardiac activity within, two chambers of the heart (e.g. both the right atrium and the right ventricle). The left atrium and left ventricle can also be paced, provided that suitable electrical contacts are effected therewith.

In general, both single and dual-chamber pacemakers are classified by type according to a three letter code. In this code, the first letter identifies the chamber of the heart that is paced (i.e., the chamber where a stimulation pulse is delivered)—with a "V" indicating the ventricle, an "A" indicating the atrium, and a "D" (dual) indicating both the atrium and ventricle. The second letter of the code identifies the chamber where cardiac activity is sensed, using the same letters to identify the atrium or ventricle or both, and where an "O" indicates that no sensing takes place.

The third letter of the code identifies the action or response that is taken by the pacemaker. In general, three types of action or responses are recognized: (1) an Inhibiting ("I") response, where a stimulation pulse is delivered to the designated chamber after a set period of time unless cardiac activity is sensed during that time, in which case the stimulation pulse is inhibited; (2) a Trigger ("T") response, where a stimulation pulse is delivered to the designated chamber of the heart a prescribed period after a sensed event; or (3) a Dual ("D") response, where both the Inhibiting mode and Trigger mode are evoked, inhibiting in one chamber of the heart and triggering in the other.

A fourth letter, "R", is sometimes added to the code to signify that the particular mode identified by the three letter code is rate-responsive, where the pacing rate may be adjusted automatically by the pacemaker based on one or more physiological factors such as blood oxygen level or the patient's activity level.

Modern pacemakers also have a great number of adjustable parameters that must be tailored to a particular patient's therapeutic needs. One adjustable parameter of particular importance in pacemakers is the pacemaker's stimulation energy. "Capture" is defined as a cardiac response to a pacemaker stimulation pulse. When a pacemaker stimulation pulse stimulates either a heart atrium or a heart ventricle during an appropriate portion of a cardiac cycle, it is desirable to have the heart properly respond to the stimulus provided. Every patient has a "capture threshold" which is generally defined as the minimum amount of stimulation energy necessary to effect capture. Capture should be achieved at the lowest possible energy setting yet provide enough of a safety margin so that, should a patient's threshold increase, the output of an implantable pacemaker, i.e., the stimulation energy, will still be sufficient to maintain capture. Dual-chamber pacemakers may have differing atrial and ventricular stimulation energy that correspond to atrial and ventricular capture thresholds, respectively.

The earliest pacemakers had a predetermined and unchangeable stimulation energy, which proved to be problematic because the capture threshold is not a static value and may be affected by a variety of physiological and other factors. For example, certain cardiac medications may temporarily raise or lower the threshold from its normal value. In another example, fibrous tissue that forms around pacemaker lead heads within several months after implantation may raise the capture threshold.

As a result, some patients eventually suffered from loss of capture as their pacemakers were unable to adjust the pre-set stimulation energy to match the changed capture thresholds. One attempted solution was to set the level of stimulation pulses fairly high so as to avoid loss of capture due to a change in the capture threshold. However, this approach resulted in some discomfort to patients who were forced to endure unnecessarily high levels of cardiac stimulation. Furthermore, such stimulation pulses consumed extra battery resources, thus shortening the useful life of the pacemaker.

When programmable pacemakers were developed, the stimulation energy was implemented as an adjustable parameter that could be set or changed by a medical practitioner. Typically, such adjustments were effected by the medical practitioner using an external programmer capable of communication with an implanted pacemaker via a magnet applied to a patient's chest or via telemetry. The particular setting for the pacemaker's stimulation energy was usually derived from the results of extensive physiological tests performed by the medical practitioner to determine the patient's capture threshold, from the patient's medical history, and from a listing of the patient's medications. While the adjustable pacing energy feature proved to be superior to the previously known fixed energy, some significant problems remained unsolved. In particular, when a patient's capture threshold changed, the patient was forced to visit the medical practitioner to adjust the pacing energy accordingly.

To address this pressing problem, pacemaker manufacturers have developed advanced pacemakers that are capable of determining a patient's capture threshold and automatically adjusting the stimulation pulses to a level just above that which is needed to maintain capture. This approach, called "autocapture", improves the patient's comfort, reduces the necessity of unscheduled visits to the medical practitioner, and greatly increases the pacemaker's battery life by conserving the energy used to generate stimulation pulses.

However, many of these advanced pacemakers require additional circuitry and/or special sensors that must be dedicated to capture verification. This requirement increases the complexity of the pacemaker system and reduces the precious space available within a pacemaker's casing, and also increases the pacemaker's cost. As a result, pacemaker manufacturers have attempted to develop automatic capture verification techniques that may be implemented in a typical programmable pacemaker without requiring additional circuitry or special dedicated sensors.

A common technique used to determine whether capture has been effected is monitoring the patient's cardiac activity and searching for the presence of an "evoked response" following a stimulation pulse. The evoked response is the response of the heart to application of a stimulation pulse. The patient's heart activity is typically monitored by the pacemaker by keeping track of the stimulation pulses delivered to the heart and examining, through the leads connected to the heart, electrical signals that are manifest concurrent with depolarization or contraction of muscle tissue (myocardial tissue) of the heart. The contraction of atrial muscle tissue is evidenced by generation of a P-wave, while the contraction of ventricular muscle tissue is evidenced by generation of an R-wave (sometimes referred to as the "QRS" complex).

When capture occurs, the evoked response is an intracardiac P-wave or R-wave that indicates contraction of the respective cardiac tissue in response to the applied stimulation pulse. For example, using such an evoked response technique, if a stimulation pulse is applied to the atrium (hereinafter referred to as an A-pulse), any response sensed by atrial sensing circuits of the pacemaker immediately following application of the A-pulse is presumed to be an evoked response that evidences capture of the atria.

However, it is for several reasons very difficult to detect a true evoked response. First, because the atrial evoked response is a relatively small signal, it may be obscured by a high energy A-pulse and therefore difficult to detect and identify. Second, the signal sensed by the pacemaker's sensing circuitry immediately following the application of a stimulation pulse may be not an evoked response but noise—either electrical noise caused, for example, by electromagnetic interference, or myocardial noise caused by random myocardial or other muscle contraction.

Another signal that interferes with the detection of an evoked response, and potentially the most difficult for which to compensate because it is usually present in varying degrees, is lead polarization. A lead/tissue interface is that point at which an electrode of the pacemaker lead contacts the cardiac tissue. Lead polarization is commonly caused by electrochemical reactions that occur at the lead/tissue interface due to application of an electrical stimulation pulse, such as an A-pulse, across the interface. Unfortunately, because the evoked response is sensed through the same lead electrodes through which the stimulation pulses are delivered, the resulting polarization signal, also referred to herein as an "afterpotential", formed at the electrode can corrupt the evoked response that is sensed by the sensing circuits. This undesirable situation occurs often because the polarization signal can be three or more orders of magnitude greater than the evoked response. Furthermore, the lead polarization signal is not easily characterized; it is a complex function of the lead materials, lead geometry, tissue impedance, stimulation energy and other variables, many of which are continually changing over time.

In each of the above cases, the result may be a false positive detection of an evoked response. Such an error leads to a false capture indication, which in turn leads to missed heartbeats—a highly undesirable and potentially life-threatening situation. Another problem results from a failure by the pacemaker to detect an evoked response that has actually occurred. In that case, a loss of capture is indicated when capture is in fact present—also an undesirable situation that will cause the pacemaker to unnecessarily invoke the pacing energy determination function in a chamber of the heart.

Automatic pacing energy determination is only invoked by the pacemaker when loss of atrial or ventricular capture is detected. An exemplary prior art automatic atrial pacing energy determination procedure is performed as follows. When loss of atrial capture is detected, the pacemaker increases the A-pulse output level to a relatively high predetermined testing level at which capture is certain to occur, and thereafter decrements the output level until atrial capture is lost. The atrial pacing energy is then set to a level slightly above the lowest output level at which atrial capture was attained. Thus, atrial capture verification is of utmost importance in proper determination of the atrial pacing energy.

When an atrial stimulation pulse is properly captured in the atrium, a subsequent ventricular contraction results in an R-wave which may be sensed through an atrial lead, in patients with intact atrioventricular ("AV") conduction, as a "far-field" signal. The far-field R-wave confirms successful atrial capture because the ventricular contraction only occurs after a properly captured atrial stimulation pulse. Previously known pacemakers have ignored this useful phenomenon because previously known single-chamber atrial pacemakers and dual-chamber pacemakers programmed to operate in an atrial mode purposefully do not sense ventricular activity through the atrial lead for a particular period of time (i.e., the "refractory" period) after delivery of the atrial stimulation pulse. Furthermore, the polarization signal formed at the atrial lead electrode may obscure and/or distort the far-field R-wave signal, even if it were sensed.

It would thus be desirable to provide a system and method for enabling the pacemaker to automatically and accurately perform atrial capture verification by sensing and identifying a far-field R-wave that occurs only after delivery by the pacemaker of a successfully captured atrial stimulation pulse. It would also be desirable to provide a system and method for reducing the negative effect of polarization and noise on capture verification by automatically isolating such negative effects from the identified far-field R-wave signal. It would further be desirable to enable the pacemaker to perform atrial capture verification without requiring dedicated circuitry and/or special sensors.

SUMMARY OF THE INVENTION

The disadvantages and limitations discussed above are overcome by the present invention. In accordance with the invention, a system and method are provided for automating verification of proper atrial capture of pacing pulses generated by a patient's implantable cardiac stimulation device by sensing and identifying a far-field ventricular signal resulting from a ventricular contraction that follows a successfully captured atrial stimulation pulse. The system and method of the present invention compensate for effects of polarization and noise on the identified far-field signal and do not require use of special dedicated circuitry or special sensors to implement the automated procedure. All of the aforesaid advantages and features are achieved without incurring any substantial relative disadvantage.

The present invention provides an implantable medical device (hereinafter "pacemaker") equipped with cardiac data acquisition capabilities. A preferred embodiment of the pacemaker of the present invention includes a control system for controlling the operation of the pacemaker, a set of leads for receiving atrial and ventricular signals and for delivering atrial and ventricular stimulation pulses, a set of sense amplifiers for sensing and amplifying the atrial and ventricular signals, a sampler, such as an A/D converter, for sampling atrial and/or ventricular signals, and pulse generators for generating the atrial and ventricular stimulation pulses. In addition, the pacemaker includes memory for storing operational parameters for the control system, such as atrial or ventricular signal sampling parameters, and atrial or ventricular signal samples. The pacemaker also includes a telemetry circuit for communicating with an external programmer.

In a preferred embodiment of the invention, the pacemaker control system periodically performs an atrial capture verification test and, when necessary, an atrial pacing threshold assessment test, which performs an assessment of the stimulation energy in the atrial chamber of the patient's heart. The frequency with which these tests are performed are preferably programmable parameters set by the medical practitioner using an external programmer when the patient is examined during an office visit or remotely via a telecommunication link. The appropriate testing frequency parameter will vary from patient to patient and depend on a number of physiologic and other factors. For example, if a patient is on a cardiac medication regimen, the patient's atrial capture threshold may fluctuate, thus requiring relatively frequent testing and adjustment of the atrial stimulation energy. Preferably, the system and method of the present invention are implemented in a pacemaker operating in an atrial mode such as AAI, AOO or AAT.

In a first embodiment of the invention, the pacemaker delivers an atrial stimulation pulse and then samples a resulting far-field ventricular signal during a predetermined far-field interval window that is centered at the expiration of a predetermined window delay. The pacemaker then compares the far-field signal sample to a predetermined far-field signal recognition template to verify whether the far-field signal sample morphology corresponds to a far-field R-wave that is expected to follow a successfully captured atrial stimulation pulse. If the far-field signal sample is approximately equal to the far-field signal recognition template, then atrial capture is deemed verified. Otherwise, the pacemaker performs an atrial stimulation energy determination procedure. This embodiment of the invention is preferably implemented in a pacemaker that is equipped with special electrodes and/or circuitry for reducing or eliminating noise and polarization signals that occur after delivery of atrial stimulation pulses.

In a second embodiment of the invention, the pacemaker delivers an atrial stimulation pulse, samples a response signal in the atrium, and then samples a resulting far-field ventricular signal during a predetermined far-field interval window that is centered at the expiration of a predetermined window delay. The response sample is then compared to the far-field sample and is compared to a predetermined far-field signal recognition template. If the sample is approximately equal to the far-field signal recognition template, then atrial capture is deemed verified. Otherwise, the pacemaker performs an atrial stimulation energy determination procedure.

Preferably, the window delay and the far-field signal recognition template are automatically determined by the pacemaker after initial implantation, and updated at other times as necessary or appropriate, as for example under the direction of the medical practitioner during a follow-up visit. In accordance with the invention, the pacemaker performs an AR conduction test to determine a conduction time and then stores the conduction time in memory. The pacemaker then delivers an atrial stimulation pulse, samples a response signal in the atrium, stores the response sample in memory, then samples a resulting far-field ventricular signal after a delay approximately equal to the conduction time and stores the far-field sample in memory.

When a predetermined number of samples and conduction times are thus acquired, the pacemaker averages each set of samples and subtracts the response sample average from the far-field signal sample average to produce a far-field signal recognition template, which is then stored in memory. The pacemaker also averages the conduction times to determine an average window delay, centers the predefined far-field interval window at the average conduction time (window delay) and stores the position of the far-field interval window in memory.

Alternately, the window delay and the far-field signal recognition template may be predefined by the medical practitioner and stored in the pacemaker memory along with the far-field interval window.

The system and method of the present invention thus automatically verify atrial capture and, when necessary, automatically determine a proper atrial stimulation energy of the patient's pacemaker, without requiring dedicated or special circuitry and/or sensors.

BRIEF DESCRIPTION OF THE DRAWINGS

The above and further features, advantages and benefits of the invention will become apparent in the following description taken in conjunction with the following drawings. It is to be understood that the foregoing general description and the following detailed description are exemplary and explanatory but are not intended to be restrictive of the invention. The accompanying drawings, which are incorporated in and constitute a part of this disclosure, illustrate several embodiments of the invention and, together with the description, serve to explain the principles of the invention in general terms. Like numerals refer to like parts throughout the disclosure.

DETAILED DESCRIPTION OF THE PREFERRED EMBODIMENTS

The system and method of the present invention utilize a pacemaker's normal sensing and control circuitry to perform automatic atrial capture verification and, when necessary, an atrial stimulation energy determination test.

The system and method of the present invention are intended for use in a single-chamber atrial pacemaker, or in a dual-chamber pacemaker programmed to operate in a single-chamber atrial pacing mode such as AOO, AAI, or AAT, and implanted in a patient who has intact atrioventricular ("AV") conduction. While the system and method of the invention are described by way of illustrative examples with specific reference to a dual-chamber pacemaker, it will thus be understood that the invention may instead be applied to a single-chamber atrial pacemaker, in which a sensing/pacing lead is connected to the atrial chamber of the heart, without departing from the spirit of the invention.

Figure 1:
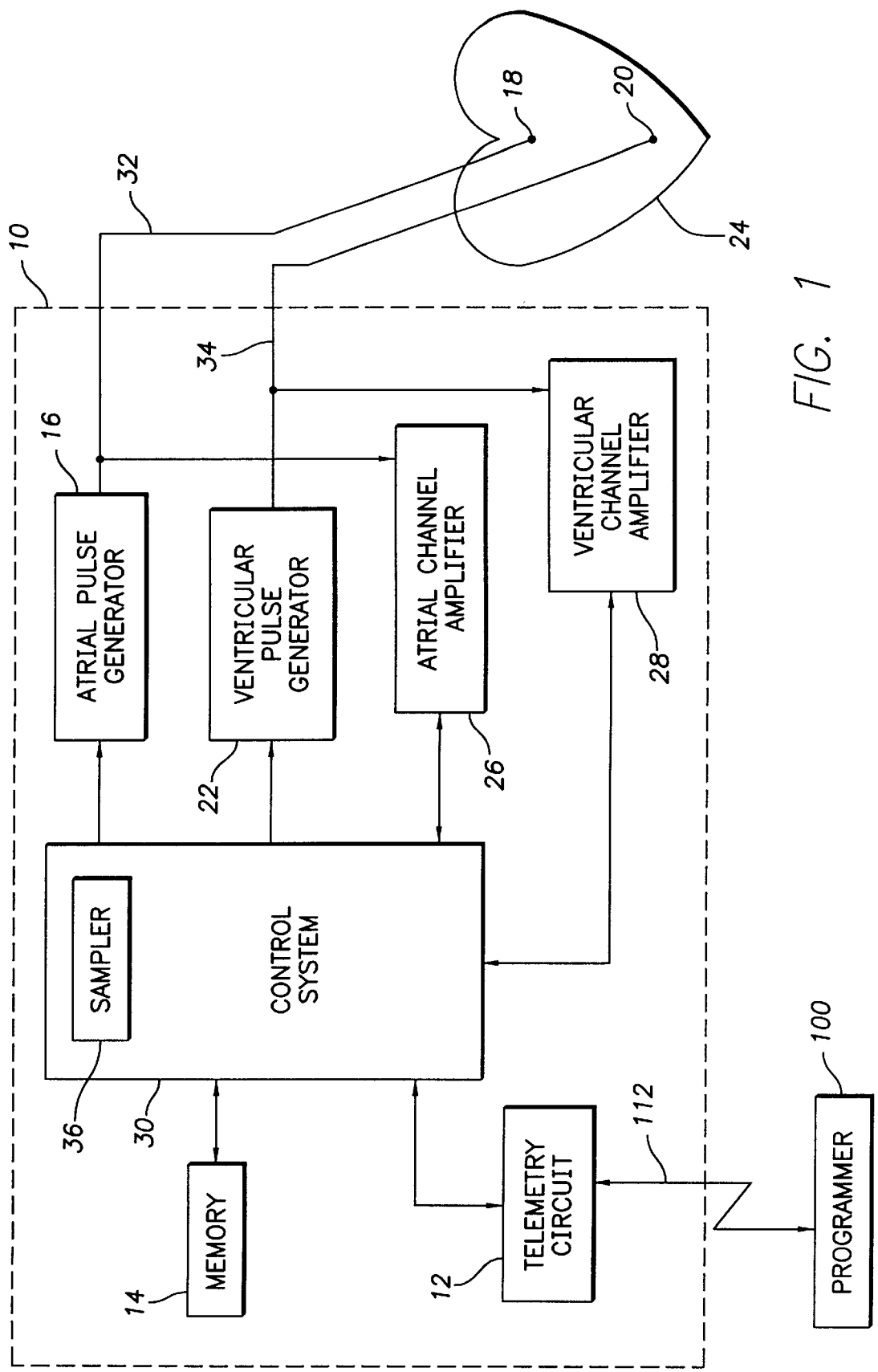
FIG. 1 is a block diagram of a dual-chamber pacemaker in accordance with the principles of the present invention.

A pacemaker 10 in accordance with the invention is shown in FIG. 1. The pacemaker 10 is coupled to a patient's heart 24 by way of leads 32 and 34, the lead 32 having an electrode 18 which is in contact with one of the atria of the heart 24, and the lead 34 having an electrode 20 which is in contact with one of the ventricles. The lead 32 carries stimulating pulses to the electrode 18 from an atrial pulse generator 16, while the lead 34 carries stimulating pulses to the electrode 20 from a ventricular pulse generator 22. In addition, electrical signals from the atria are carried from the electrode 18, through the lead 32, to the input terminal of an atrial channel amplifier 26. Electrical signals from the ventricles are carried from the electrode 20, through the lead 34 to the input terminal of a ventricular channel amplifier 28.

Operatively controlling the dual-chamber pacemaker 10 is a control system 30. The control system 30 is preferably a microprocessor-based system such for example as that disclosed in commonly-assigned U.S. Pat. No. 4,940,052 of Mann, which is incorporated herein by reference in its entirety. The control system 30 may also be a state logic-based system such for example as that disclosed in commonly assigned U.S. Pat. No. 4,944,298 of Sholder, which is also incorporated herein by reference in its entirety. The control system 30 includes a real-time clock (not shown) providing timing functionality for monitoring cardiac events and for timing the application of therapeutic pulses by the pulse generators 16 and 24. The control system 30 also includes a sampler 36, such as an A/D converter, for generating digital signals representative of cardiac activity by sampling the atrial and/or ventricular cardiac signals acquired by the respective amplifiers 26 and 28. Alternately, the sampler 36 may be implemented separately from the control system 30 and connected directly to the amplifiers 26 and 28.

The pacemaker 10 also includes a memory 14 which is coupled to the control system 30. The memory 14 allows certain control parameters used by the control system 30 in controlling the operation of the pacemaker 10 to be programmably stored and modified, as required, to customize the operation of the pacemaker 10 to suit the needs of a particular patient. In particular, parameters regulating the operation of the sampler 36 are stored in the memory 14. In addition, samples acquired by the sampler 36 may be stored in the memory 14 for later analysis by the control system 30.

The control system 30 receives the output signals from the atrial channel amplifier 26. Similarly, the control system 30 also receives the output signals from the ventricular channel amplifier 28. These various output signals are generated each time that an atrial event (e.g. a P-wave) or a ventricular event (e.g. an R-wave) is sensed within the heart 24.

The control system 30 also generates an atrial trigger signal that is sent to the atrial pulse generator 16, and a ventricular trigger signal that is sent to the ventricular pulse generator 22. These trigger signals are generated each time that a stimulation pulse is to be generated by one of the pulse generators 16 or 22. The atrial stimulation pulse is referred to simply as the "A-pulse", and the ventricular stimulation pulse is referred to as the "V-pulse". The characteristics of these stimulation pulses are determined by pacing energy settings that are among the parameters stored in the memory 14. The control system 30 may also be programmed to operate the pacemaker 10 in a variety of pacing and sensing modes. Preferably, the control system 30 is programmed to a single-chamber atrial mode such as AOO, AAI, or AAT.

A telemetry circuit 12 is further included in the pacemaker 10 and connected to the control system 30. The telemetry circuit 12 may be selectively coupled to an external programmer 100 by means of an appropriate communication link 112, such as an electromagnetic telemetry link or a remote communication link such as a pair of modems interconnected via a telecommunications link and equipped with telemetry capabilities.

The operation of the pacemaker 10 is generally controlled by a control program stored in the memory 14 and executed by the control system 30. This control program typically consists of multiple integrated program modules, with each module bearing responsibility for controlling one or more functions of the pacemaker 10. For example, one program module may control the delivery of stimulating pulses to the heart 24, while another may control the verification of atrial capture and atrial pacing energy determination. In effect, each program module is a control program dedicated to a specific function or set of functions of the pacemaker 10.

Figure 2:
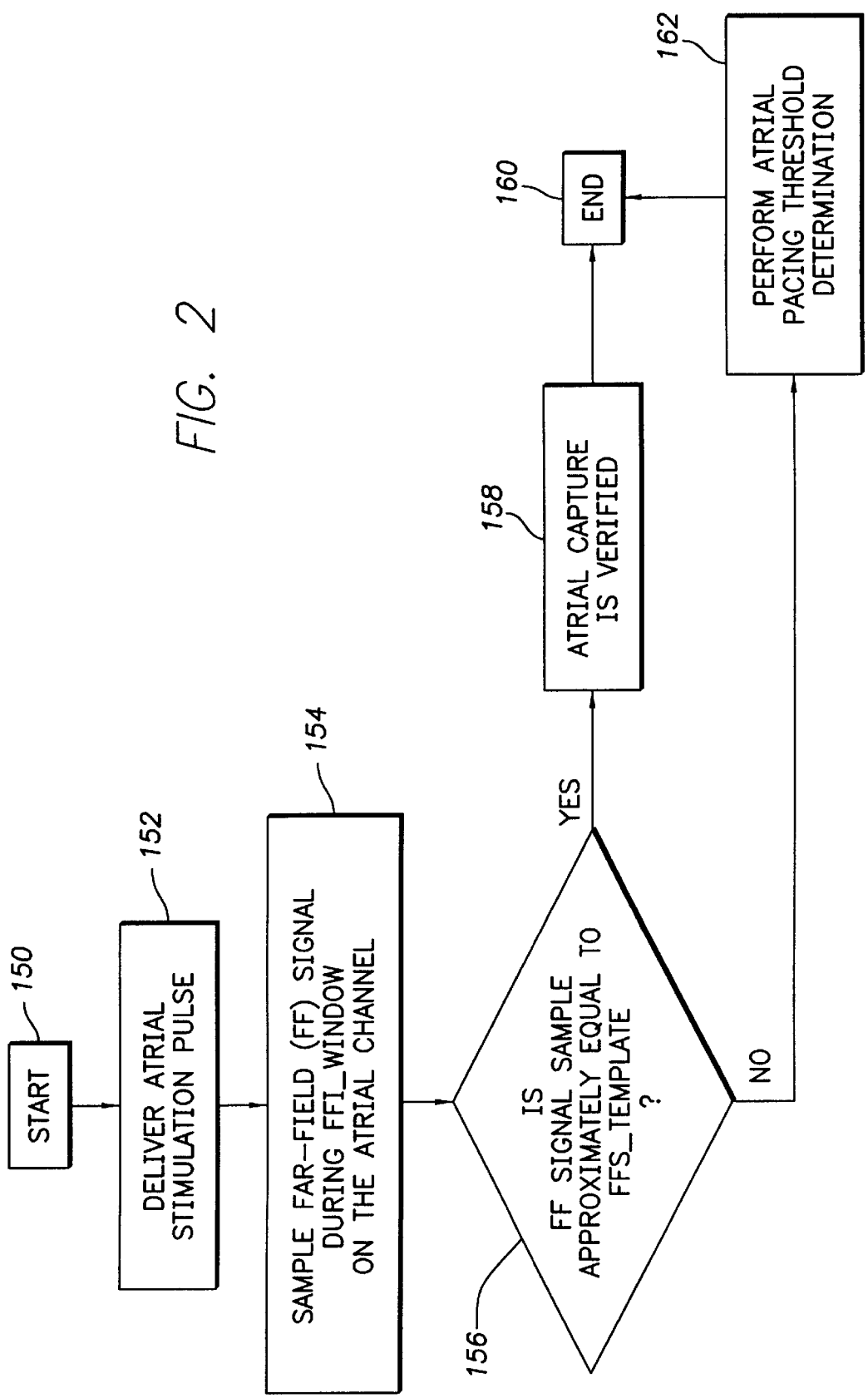
FIG. 2 is a logic flow diagram of a first embodiment of an automatic atrial capture verification and atrial stimulation energy determination control program executed by the control system of the pacemaker of FIG. 1, in accordance with the principles of the present invention.

FIG. 2 depicts a logic flow diagram representing a first embodiment of a control program for controlling the atrial capture verification and atrial pacing energy determination procedure executed by the control system 30 in accordance with the present invention. The control program of FIG. 2 is preferably used in a pacemaker that is equipped with special electrodes and/or circuitry for reducing or eliminating noise and polarization signals that occur after delivery of stimulation pulses.

Preferably, the control system 30 periodically invokes the control program to perform the capture verification test and, when necessary or appropriate, the atrial pacing energy assessment test in the atrial chamber of the heart 24. The frequency with which these tests are to be performed are preferably programmable parameters set by the medical practitioner using the external programmer 100 when the patient is examined during an office visit or remotely via the communication link 112. The appropriate testing frequency parameter will vary from patient to patient and depend on a number of physiologic and other factors. For example, if a patient is on a cardiac medication regimen, the patient's atrial capture threshold may fluctuate, thus requiring relatively frequent testing and adjustment of the atrial pacing energy.

After the atrial capture verification test begins at a step 150, the control system 30 at a step 152 causes the atrial pulse generator 16 to deliver a stimulation pulse to the atrial chamber. Typically, the atrial stimulation pulse triggers a subsequent ventricular contraction resulting in a ventricular R-wave that is sensed by the atrial channel amplifier 26 through the atrial lead 32 as a far-field signal. The lack of a ventricular contraction subsequent to the delivery of the atrial stimulation pulse commonly indicates absence of atrial capture.

At a step 154, the control system 30 samples the far-field signal via the sampler 36 during a predefined far-field interval window ("FFI_WINDOW"). The FFI_WINDOW is preferably "centered" at the expiration of an expected window delay between the delivery of the atrial stimulation pulse and generation of the far-field signal. For example, if the expected window delay is 20 ms, and the FFI_WINDOW is defined to be 10 ms, then the FFI_WINDOW will begin 15 ms after delivery of the atrial stimulation pulse, and will end 10 ms later (i.e., 25 ms after the delivery of the pulse). This expected window delay is approximately equal to AV conduction time. While it is expected that the far-field signal will occur at approximately the expiration of the window delay, it is possible that for a variety of reasons the far-field signal actually occurs shortly before or shortly after the delay. The purpose of the FFI_WINDOW is thus to provide an opportunity for the control system 30 to sense a far-field signal that does not occur exactly after the expected window delay. A control program module for automatically determining the expected window delay and centering the FFI_WINDOW at the expected window delay is described below in connection with FIGS. 4 and 5.

At a test 156, the control system 30 compares the far-field signal sample obtained at the step 154 with a far-field signal recognition template ("FFS_TEMPLATE") stored in the memory 14 to determine whether the far-field signal sample is approximately equal to the FFS_TEMPLATE. The FFS_TEMPLATE is preferably representative of a morphology of a typical far-field signal that occurs in the patient's heart 24. The FFS_TEMPLATE may be supplied by the medical practitioner using the programmer 100 or, preferably, may be automatically determined by the control system 30. The control program module described below in connection with FIGS. 4 and 5 demonstrates an advantageous and preferred technique for automatically determining the FFS_TEMPLATE.

If it is determined at the test 156 that the far-field signal sample is approximately equal to the FFS_TEMPLATE, then at a step 158 atrial capture is deemed to have been verified, and the control program ends at a step 160. If, on the other hand, the far-field signal sample is not approximately equal to the FFS_TEMPLATE, then at a step 162 the control system 30 performs an atrial pacing energy determination procedure. Various advantageous and appropriate atrial pacing energy determination procedures are well known in the art and will not therefore be described herein.

Figure 3:
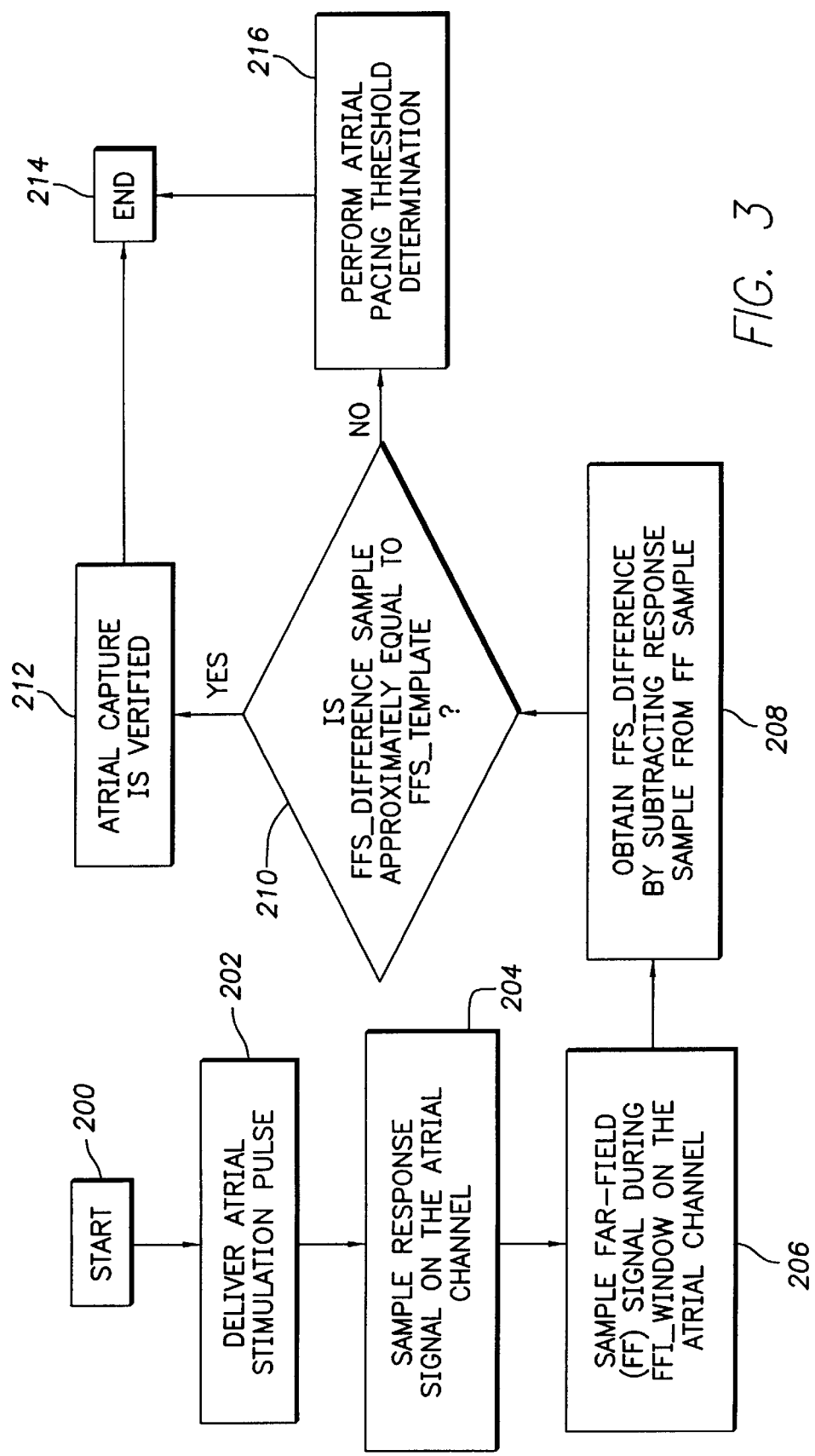
FIG. 3 is a logic flow diagram of a second embodiment of an automatic atrial capture verification and atrial pacing threshold determination control program executed by the control system of the pacemaker of FIG. 1, in accordance with the principles of the present invention.

FIG. 3 depicts a logic flow diagram representing a second embodiment of a control program for controlling the atrial capture verification and atrial pacing energy determination procedure executed by the control system 30 in accordance with the present invention. Unlike the control program of FIG. 2, the control program of FIG. 3 may be used in a pacemaker that is not equipped with special electrodes and/or circuitry for reducing or eliminating polarization signals that occur after delivery of stimulation pulses. As with the previously described control program of FIG. 2, the control system 30 periodically invokes the alternative control program of FIG. 3 to perform the capture verification test and, when necessary, the atrial pacing energy assessment test in the atrial chamber of the heart 24.

After the atrial capture verification test of FIG. 3 begins at a step 200, the control system 30 at a step 202 causes the atrial pulse generator 16 to deliver a stimulation pulse to the atrial chamber. When delivered, the atrial stimulation pulse triggers a response signal in the atrial chamber that may consist of an evoked response representative of an atrial contraction combined with a polarization signal and other noise. Typically, the atrial stimulation pulse also triggers a subsequent ventricular contraction resulting in a ventricular R-wave that is sensed by the atrial channel amplifier 26 through the atrial lead 32 as a far-field signal. The lack of a ventricular contraction subsequent to the delivery of the atrial stimulation pulse commonly indicates absence of atrial capture.

At a step 204, the control system 30 samples the response signal via the sampler 36 and, at a step 206, also samples the far-field signal via the sampler 36 during a predefined FFI_WINDOW. As was previously described in connection with FIG. 2, the FFI_WINDOW is preferably "centered" at the expiration of the expected window delay between the delivery of the atrial stimulation pulse and generation of the far-field signal.

At a step 208, the control system 30 obtains a far-field signal difference ("FFS_DIFFERENCE") by subtracting the response sample obtained at the step 204 from the far-field signal sample obtained at the step 206. The FFS_DIFFERENCE is representative of a true far-field signal without the distorting effects of an overlapping atrial response, such as polarization.

At a test 210, the control system 30 compares the FFS_DIFFERENCE with the FFS_TEMPLATE stored in the memory 14 to determine whether the true far-field signal sample (as represented by the FFS_DIFFERENCE) is approximately equal to the FFS_TEMPLATE. As was previously discussed, the FFS_TEMPLATE may be supplied by the medical practitioner using the programmer 100 or, preferably, may be automatically determined by the control system 30. The control program module described below in connection with FIGS. 4 and 5 provides an advantageous technique for automatically determining the FFS_TEMPLATE.

If it is determined at the test 210 that the FFS_DIFFERENCE is approximately equal to the FFS_TEMPLATE, then at a step 212 atrial capture is deemed to have been verified, and the control program ends at a step 214. If, on the other hand, the FFS_DIFFERENCE is not approximately equal to the FFS_TEMPLATE, then at a step 216 the control system 30 performs an atrial pacing energy determination procedure. Various advantageous and appropriate atrial pacing energy determination procedures are well known in the art and will not therefore be described herein.

Figure 4:
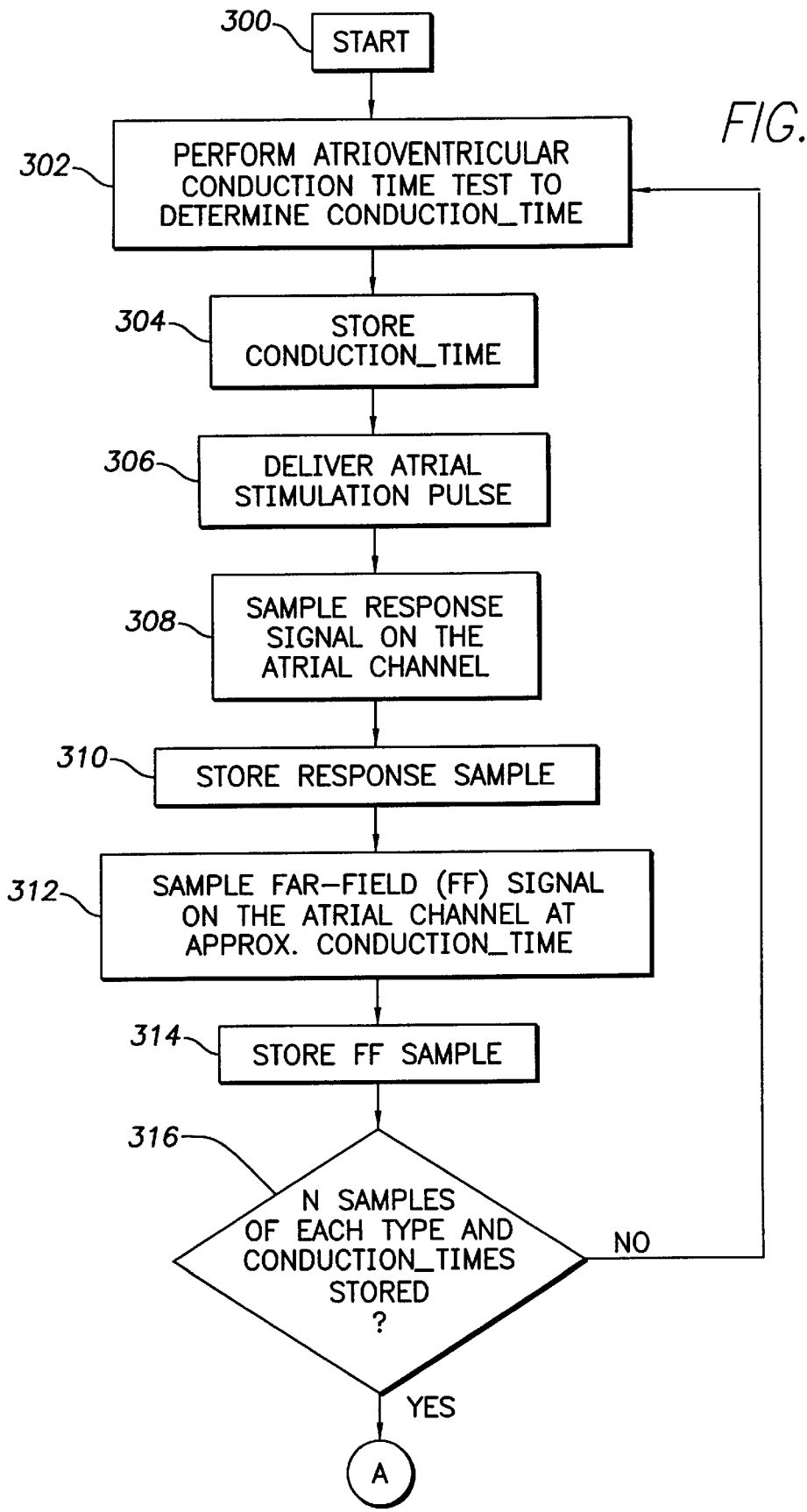
FIGS. 4 and 5 is a logic flow diagram of an automatic far-field interval window and far-field signal recognition template determination program executed by the control system of the pacemaker of FIG. 1, in accordance with the principles of the present invention.
Figure 5:
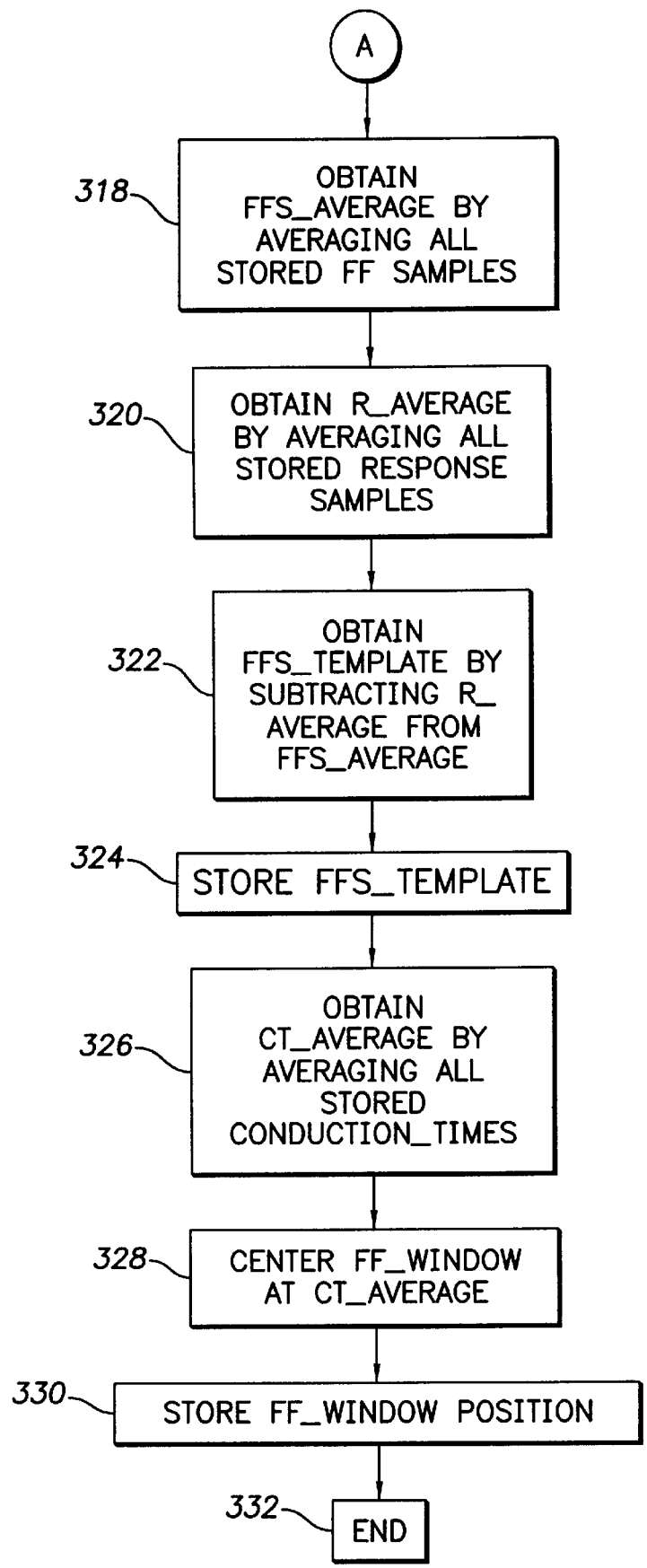

FIGS. 4 and 5 depicts a logic flow diagram representing a preferred embodiment of a control program module for automatically determining the expected delay and the centering of the FFI_WINDOW at the expected delay, and for automatically determining the FFS_TEMPLATE. After the control program module begins at a step 300, the control system 30 at a step 302 performs an AV conduction test to determine the expected delay ("CONDUCTION_TIME") between the delivery of the atrial stimulation pulse and the sensing of the far-field R-wave signal by the atrial channel amplifier 26. As was previously described, the expected delay is equivalent to AV conduction time. Various advantageous and appropriate AV conduction time measurement procedures are well known in the art and will not therefore be described herein. At a step 304, the control system 30 stores the thereby determined CONDUCTION_TIME in the memory 14.

At a step 306, the control system 30 causes the atrial pulse generator 16 to deliver a stimulation pulse to the atrial chamber of the heart 24. When delivered, the atrial stimulation pulse triggers a response signal in the atrial chamber that may consist of an evoked response representative of an atrial contraction combined with a polarization signal. Typically, the atrial stimulation pulse also triggers a subsequent ventricular contraction resulting in a ventricular R-wave that is sensed by the atrial channel amplifier 26 through the atrial lead 32 as a far-field signal.

At a step 308, the control system 30 samples the response signal via the sampler 36, and at a step 310 stores the response sample in the memory 14. At a step 312, the control system 30 samples the far-field signal via the sampler 36 after a delay, following the delivery of the atrial stimulation pulse at the step 306, approximately equal to the CONDUCTION_TIME. At a step 314, the control system 30 stores the far-field signal sample in the memory 14.

At a test 316, the control system 30 determines whether a predetermined number (hereinafter "N") of each of the response samples, far-field signal samples, and CONDUCTION_TIMEs are stored in the memory 14. The parameter N may be selected by the medical practitioner using the programmer 100. In order to increase precision of the FF_WINDOW positioning and to improve the accuracy of the FFS_TEMPLATE, N should be set to a sufficient number of samples to accurately classify the conduction time (e.g., three samples or more).

If N CONDUCTION_TIMES and samples of each type have not been stored, then the control system 30 returns from the step 316 to the step 302 to perform the AV conduction test. Thus, the control system 30 repeats the steps 302 through 314 until N CONDUCTION_TIMEs and N samples of each type have been stored in the memory 14. When N CONDUCTION_TIMEs and N samples of each type have been stored, at a step 318 the control system 30 determines a FFS_AVERAGE representative of an average far-field signal sample by averaging all of the stored far-field signal samples, and optionally stores the FFS_AVERAGE in the memory 14. At a step 320, the control system 30 similarly determines an R_AVERAGE representative of an average response sample by averaging all of the stored response samples, and optionally stores the calculated R_AVERAGE in the memory 14.

At a step 322, the control system 30 determines the FFS_TEMPLATE representative of a true far-field signal by subtracting R_AVERAGE from FFS_AVERAGE. Because FFS_AVERAGE represents the average far-field signal whereas the raw detected far-field signal may be mixed with the response signal, subtracting the R_AVERAGE (representative of just the response signal including polarization and other noise) from the FFS_AVERAGE results in a representation of the true far-field signal. At a step 324, the FFS_TEMPLATE is stored in the memory 14, so that it is available for future identification of a far-field signal during atrial capture verification as described above in connection with FIGS. 2–3.

At a step 326, the control system 30 determines an average expected delay value CT_AVERAGE by averaging all CONDUCTION_TIMEs stored in the memory 14 and, at a step 328, centers the predefined FF_WINDOW at the CT_AVERAGE. At a step 330, the control system 30 stores the FF_WINDOW position to increase the capability of the atrial channel amplifier 26 to sense far-field signals that occur before or after the expected delay, and then ends the control program module at a step 332.

One skilled in the art will appreciate that the present invention can be practiced by other than the described embodiments, which are presented for purposes of illustration and not of limitation, and that the present invention is limited only by the claims that follow.

What is claimed is:

1. A system for detecting capture in an atrial chamber of a patient's heart and implemented in an implantable pacemaker implanted in the patient and connected to the atrial chamber via a lead, the system comprising:

pulse generating means for generating a stimulation pulse for delivery to the atrial chamber through the lead to trigger a subsequent contraction in a ventricular chamber of the heart so as to produce a far-field signal;

first sampling means for generating a far-field signal sample by sampling the produced far-field signal during a far-field interval window;

window generating means for periodically determining the far-field interval window; and first control means for comparing the far-field signal sample to a predetermined far-field signal recognition template, such that:
   (i) when the far-field signal sample is approximately equal to the predetermined far-field signal recognition template, the first control means generates a first signal indicative of presence of atrial capture, and
   (ii) when the far-field signal sample is not approximately equal to the predetermined far-field signal recognition template, the first control means generates a second signal indicative of absence of atrial capture.

2. The system of claim 1, further comprising sensing means, connected to the lead and to the first sampling means, for sensing the produced far-field signal through the lead.

3. The system of claim 1, wherein the far-field interval window is sized so as to be of sufficient duration to accommodate sampling of the produced far-field signal when the subsequent ventricular contraction occurs within a predetermined period after the stimulation pulse is generated.

4. The system of claim 3, wherein the window generating means for periodically determining the far-field interval window comprises:

testing means for determining an approximate AV conduction time value by performing an atrioventricular conduction test in the heart;

first memory means for storing the determined approximate conduction time value; and second control means for:
   (i) repeatedly and sequentially triggering the testing means and the first memory means to generate and store by the first memory means a predetermined plurality of the AV conduction time values;
   (ii) determining an average AV conduction time value by averaging the plural AV conduction time values; and
   (iii) defining a time interval defining the far-field interval window having a predetermined duration and positioning the far-field interval window so that the time interval is substantially centered at a time delay measured from the generation of the stimulation pulse, the delay being approximately equal to the average AV conduction time value.

5. The system of claim 4, further comprising template generating means for generating the predetermined far-field signal recognition template, the template generating means comprising:

third control means for causing the pulse generating means to generate a stimulation pulse for delivery to the atrial chamber through the lead so as to:
        (i) produce a response signal in the atrial chamber, and
        (ii) produce the far-field signal caused by the subsequently triggered contraction in the ventricular chamber of the heart;

second sampling means for:
        (i) generating a response sample by sampling the response signal; and
        (ii) generating a far-field signal sample by sampling the far-field signal after a time delay following the generation of the stimulation pulse, the delay being substantially equal to the predetermined AV conduction time value;

second memory means for storing the response sample and far-field signal sample; and fourth control means for:
        (i) repeatedly and sequentially triggering the third control means, the second sampling means, and the second memory means to generate and store by the second memory means a predetermined plurality of the response samples and a predetermined plurality of the far-field signal samples;
        (ii) determining an average response by averaging the plural response samples;
        (iii) determining an average far-field signal by averaging the plural far-field signal samples; and
        (iv) determining the far-field signal recognition template by comparing the average response from the average far-field signal.

6. The system of claim 1, further comprising: pacing energy determination means responsive to the first control means for determining, when the first control means generates the second signal, an atrial pacing energy in the atrial chamber.

7. A system for determining a far-field signal recognition template for use in identification of a far-field signal originating from a ventricle of a patient's heart, the system being implemented in an implantable pacemaker implanted in the patient and connected to the atrial chamber via a lead, the system comprising:

pulse generating means for generating a stimulation pulse for delivery to the atrial chamber through the lead so as to:
        (i) produce a response signal in the atrial chamber, and
        (ii) produce a far-field signal caused by a subsequently triggered contraction in a ventricular chamber of the heart;

sampling means for:
        (i) generating a response sample by sampling the produced response signal; and
        (ii) generating a far-field signal sample by sampling the produced far-field signal after a delay following the generation of the stimulation pulse, the delay being substantially equal to a predefined AV conduction time value;

memory means for storing the produced response and far-field signal samples; and control means for:
        (i) repeatedly and sequentially triggering the pulse generating means, the sampling means, and the memory means to generate and store by the memory means a predetermined plurality of the response samples and a predetermined plurality of the far-field signal samples;
        (ii) determining an average response by averaging the plural response samples;
        (iii) determining an average far-field signal by averaging the plural far-field signal samples; and
        (iv) determining a far-field signal recognition template by comparing the average response from the average far-field signal.

8. The system of claim 7, further comprising sensing means, connected to the lead and to the first sampling means, for sensing the produced far-field signal through the lead.

9. A system for detecting capture in an atrial chamber of a patient's heart and implemented in an implantable pacemaker implanted in the patient and connected to the atrial chamber via a lead, the system comprising:

a pulse generator that generates a stimulation pulse for delivery to the atrial chamber through the lead to trigger a subsequent contraction in a ventricular chamber of the heart so as to produce a far-field signal;

a signal sampler operatively connected to the pulse generator, that generates a far-field signal sample by sampling the produced far-field signal during a far-field interval window;

a window generator for periodically determining the far-field interval window; and a controller operatively connected to the pulse generator and the signal sampler that compares the far-field signal sample to a predetermined far-field signal recognition template, such that:
        (i) when the far-field signal sample is approximately equal to the predetermined far-field signal recognition template, the controller generates a first signal indicative of presence of atrial capture, and
        (ii) when the far-field signal sample is not approximately equal to the predetermined far-field signal recognition template, the controller generates a second signal indicative of absence of atrial capture.

10. The system of claim 9, further comprising a sensor, operatively connected to the lead and to the first signal sampler, that senses the produced far-field signal through the lead.

11. The system of claim 9, wherein the far-field interval window is sized so as to be of sufficient duration to accommodate sampling of the produced far-field signal when the subsequent ventricular contraction occurs within a predetermined period after the stimulation pulse is generated.

12. The system of claim 9, further comprising stimulation energy determination circuitry operatively connected to the controller that determines, when the controller generates the second signal, an atrial stimulation energy in the atrial chamber.

13. The system of claim 9 wherein the window generator comprises testing circuitry that determines an approximate AV conduction time value by performing an atrioventricular conduction test in the heart and a memory that stores the determined approximate conduction time value, and wherein the window generator is operable to cause the controller to:

(i) repeatedly and sequentially trigger the testing circuitry and the memory to generate and store in the memory a predetermined plurality of the AV conduction time values;
    (ii) determine an average AV conduction time value by averaging the plural AV conduction time values; and (iii) define a time interval defining the far-field interval window having a predetermined duration and positioning the far-field interval window so that the time interval is substantially centered at a time delay measured from the generation of the stimulation pulse, the delay being approximately equal to the average AV conduction time value.

14. (Amended) The system of claim 9, further comprising a template generator that generates the predetermined far-field signal recognition template, the template generator comprising:

a memory; and pulse trigger circuitry operable to cause the pulse generator to generate a stimulation pulse for delivery to the atrial chamber through the lead so as to:
  (i) produce a response signal in the atrial chamber, and
  (ii) produce a far-field signal caused by the subsequently triggered contraction in the ventricular chamber of the heart;

sampling trigger circuitry operable to cause the signal sampler to:
  (i) generate a response sample by sampling the response signal; and
  (ii) generate a far-field signal sample by sampling the far-field signal after a time delay following the generation of the stimulation pulse, the delay being substantially equal to a predetermined AV conduction time value; and wherein the template generator is operable to cause the controller to:
  (i) repeatedly and sequentially trigger the pulse trigger circuitry, the sampling trigger circuitry and the memory, to generate and store in the memory a predetermined plurality of the response samples and a predetermined plurality of the far-field signal samples;
  (ii) determine an average response by averaging the plural response samples;
  (iii) determine an average far-field signal by averaging the plural far-field signal samples; and
  (iv) determine the far-field signal recognition template by comparing the average response from the average far-field signal.

15. A system for determining a far-field signal recognition template for use in identification of a far-field signal originating from a ventricle of a patient's heart, the system being implemented in an implantable pacemaker implanted in the patient and connected to the atrial chamber via a lead, the system comprising:

a pulse generator that generates a stimulation pulse for delivery to the atrial chamber through the lead so as to:
  (i) produce a response signal in the atrial chamber, and
  (ii) produce a far-field signal caused by a subsequently triggered contraction in a ventricular chamber of the heart;

a signal sampler that:
  (i) generates a response sample by sampling the produced response signal; and
  (ii) generates a far-field signal sample by sampling the produced far-field signal after a delay following the generation of the stimulation pulse, the delay being substantially equal to a predefined AV conduction time value;

a memory that stores the response and far-field signal samples; and a controller that:
  (i) repeatedly and sequentially triggers the pulse generator, the signal sampler, and the memory to generate and store in the memory a predetermined plurality of the response samples and a predetermined plurality of the far-field signal samples;
  (ii) determines an average response by averaging the plural response samples;
  (iii) determines an average far-field signal by averaging the plural far-field signal samples; and
  (iv) determines the far-field signal recognition template by comparing the average response from the average far-field signal.

16. The system of claim 15, further comprising a sensor, connected to the lead and to the signal sampler, for sensing the produced far-field signal through the lead.

17. A method for detecting capture in an atrial chamber of a patient's heart and implemented in an implantable pacemaker implanted in the patient and connected to the atrial chamber via a lead, the method comprising the steps of:

(a) generating, by a pulse generator, a stimulation pulse for delivery to the atrial chamber through the lead to trigger a subsequent contraction in a ventricular chamber of the heart so as to produce a far-field signal;

(b) generating, by a signal sampler, a far-field signal sample by sampling the produced far-field signal during a far-field interval window, wherein the far-field interval window is periodically determined; and (c) comparing, by a controller, the far-field signal sample to a predetermined far-field signal recognition template, and
  (1) when the far-field signal sample is approximately equal to the predetermined far-field signal recognition template, generating a first signal indicative of presence of atrial capture, and
  (2) when the far-field signal sample is not approximately equal to the predetermined far-field signal recognition template, generating a second signal indicative of absence of atrial capture.

18. The method of claim 17, further comprising a step following step (a) of sensing the produced far-field signal by a sensor and through the lead.

19. The method of claim 17, wherein the far-field interval window is sized so as to be of sufficient duration to accommodate sampling of the produced far-field signal when the subsequent ventricular contraction occurs within a predetermined period after step (a).

20. The method of claim 17, further comprising the step of, when the second signal is generated at step (c), determining, by stimulation energy determination circuitry, an atrial stimulation energy.

21. The method of claim 17, further comprising the steps of:

(d) determining, by the controller, an approximate AV conduction time value by performing an atrioventricular conduction test in the heart;

(e) storing, in a memory, the determined approximate conduction time value;

(f) generating a predetermined plurality of stored AV conduction time values by repeating, by the controller, steps (d) through (e) for a predetermined number of repetitions;

(g) determining, by the controller, an average AV conduction time value by averaging the plural AV conduction time values; and (h) determining, by the controller, a time interval defining the far-field interval window having a duration and positioning the far-field interval window so that the time interval is substantially centered at a time delay measured from the generation of the stimulation pulse at step (a), the delay being approximately equal to the average AV conduction time value.

22. The method of claim 17, further comprising the steps of:

(i) generating, by the pulse generator prior to step (a), a stimulation pulse for delivery to the atrial chamber through the lead so as to:
   (1) produce a response signal in the atrial chamber, and
   (2) produce the far-field signal caused by the subsequently triggered contraction in the ventricular chamber of the heart;

(j) generating, by the signal sampler, a response sample by sampling the produced response signal;

(k) generating, by the signal sampler, a far-field signal sample by sampling the produced far-field signal after a delay following step (a), the delay being substantially equal to a predetermined AV conduction time value;

(l) storing, in a memory, the response and far-field signal samples;

(m) generating, a predetermined plurality of the stored response samples and a predetermined plurality of the stored far-field signal samples by repeating, by the controller, steps (i) through (l) for a predetermined number of repetitions;

(n) determining, by the controller, an average response by averaging the plural response samples;

(o) determining, by the controller, an average far-field signal by averaging the plural far-field signal samples; and (p) determining, by the controller, the far-field signal recognition template by subtracting the average response from the average far-field signal.

23. A method for determining a far-field signal recognition template for use in identification of a far-field signal originating from a ventricle of a patient's heart, the method being implemented in an implantable pacemaker implanted in the patient and connected to the atrial chamber via a lead, the method comprising the steps of:

(a) generating, by a pulse generator, a stimulation pulse for delivery to the atrial chamber through the lead so as to:
   (1) produce a response signal in the atrial chamber, and
   (2) produce a far-field signal caused by a subsequently triggered contraction in a ventricular chamber of the heart;

(b) generating, by a signal sampler, a response sample by sampling the produced response signal;

(c) generating, by the signal sampler, a far-field signal sample by sampling the produced far-field signal after a delay following step (a), the delay being substantially equal to a predetermined AV conduction time value;

(d) storing, in a memory, the response and far-field signal samples;

(e) generating, a predetermined plurality of the stored response samples and a predetermined plurality of the stored far-field signal samples by repeating, by a controller, steps (a) through (d) for a predetermined number of repetitions;

(f) determining, by the controller, an average response by averaging the plural response samples;

(g) determining, by the controller, an average far-field signal by averaging the plural far-field signal samples; and (h) determining, by the controller, the far-field signal recognition template by subtracting the average response from the average far-field signal.

24. The method of claim 23, further comprising a step of sensing after step (a), by a sensor and through the lead, the produced far-field signal.

25. A system for detecting capture in an atrial chamber of a patient's heart and implemented in an implantable pacemaker implanted in the patient and connected to the atrial chamber via a lead, the system comprising:

a pulse generator that generates a stimulation pulse for delivery to the atrial chamber through the lead to trigger a subsequent contraction in a ventricular chamber of the heart so as to produce a far-field signal;

a signal sampler operatively connected to the pulse generator, that generates a far-field signal sample by sampling the produced far-field signal during a predetermined far-field interval window;

a template generator for periodically determining a far-field signal recognition template; and a controller operatively connected to the pulse generator and the signal sampler that compares the far-field signal sample to the far-field signal recognition template, such that:
   (i) when the far-field signal sample is approximately equal to the far-field signal recognition template, the controller generates a first signal indicative of presence of atrial capture, and
   (ii) when the far-field signal sample is not approximately equal to the far-field signal recognition template, the controller generates a second signal indicative of absence of atrial capture.

26. The system of claim 25 further comprising a sensor, operatively connected to the lead and to the first signal sampler, that senses the produced far-field signal through the lead.

27. The system of claim 25 wherein the predetermined far-field interval window is sized so as to be of sufficient duration to accommodate sampling of the produced far-field signal when the subsequent ventricular contraction occurs within a predetermined period after the stimulation pulse is generated.

28. The system of claim 25 further comprising stimulation energy determination circuitry operatively connected to the controller that determines, when the controller generates the second signal, an atrial stimulation energy in the atrial chamber.

29. The system of claim 25 further comprising a window generator that generates the predetermined far-field window, the window generator comprising testing circuitry that determines an approximate AV conduction time value by performing an atrioventricular conduction test in the heart and a memory that stores the determined approximate conduction time value, wherein the window generator is operable to cause the controller to:

(i) repeatedly and sequentially trigger the testing circuitry and the memory to generate and store in the memory a predetermined plurality of the AV conduction time values;

(ii) determine an average AV conduction time value by averaging the plural AV conduction time values; and (iii) define a time interval defining the far-field interval window having a predetermined duration and positioning the far-field interval window so that the time interval is substantially centered at a time delay measured from the generation of the stimulation pulse, the delay being approximately equal to the average AV conduction time value.

30. The system of claim 25 wherein the template generator comprises:

pulse trigger circuitry operable to cause the pulse generator to generate a stimulation pulse for delivery to the atrial chamber through the lead so as to:
(i) produce a response signal in the atrial chamber, and
(ii) produce a far-field signal caused by the subsequently triggered contraction in the ventricular chamber of the heart;

sampling trigger circuitry operable to cause the signal sampler to:
(i) generate a response sample by sampling the response signal; and
(ii) generate a far-field signal sample by sampling the far-field signal after a time delay following the generation of the stimulation pulse, the delay being substantially equal to a predetermined AV conduction time value; and wherein the template generator is operable to cause the controller to:
(i) repeatedly and sequentially trigger the pulse trigger circuitry, the sampling trigger circuitry, and the memory to generate and store in the memory a predetermined plurality of the response samples and a predetermined plurality of the far-field signal samples;
(ii) determine an average response by averaging the plural response samples;
(iii) determine an average far-field signal by averaging the plural far-field signal samples; and
(iv) determine the far-field signal recognition template by comparing the average response from the average far-field signal.

* * * * *